US005756439A

United States Patent [19]

He et al.

[11] Patent Number: 5,756,439

[45] Date of Patent: May 26, 1998

[54] LIQUID COMPOSITIONS COMPRISING COPOLYMER MILDNESS ACTIVES

[75] Inventors: Mengtao He, Wayne; Michael Fair, Hackensack, both of N.J.; Michael Massaro, Congers, N.Y.

[73] Assignee: Lever Brothers Company, Division of Conopco, Inc., New York, N.Y.

[21] Appl. No.: 616,945

[22] Filed: Mar. 18, 1996

[51] Int. Cl.[6] .................................................. A61K 31/075

[52] U.S. Cl. ......................... 510/159; 510/413; 510/421; 510/506

[58] Field of Search .................................... 510/159, 413, 510/421, 506

[56] References Cited

U.S. PATENT DOCUMENTS 5,064,640 11/1991 Kleber et al. ............................ 424/52
5,073,363 12/1991 Pellico ...................................... 424/49
5,230,824 7/1993 Carlson, Sr. et al. ............. 252/174.21
5,368,845 11/1994 Gaffar et al. ............................... 424/54
5,604,189 2/1997 Zhang et al. ............................ 510/112

OTHER PUBLICATIONS

McCutcheon's Emulsifiers & Detergents North America Ed.; N.J. 1983, p. 203.

*Primary Examiner*—Margaret Medley
*Attorney, Agent, or Firm*—Ronald A. Koatz

[57] ABSTRACT

The present invention relates to liquid detergent compositions comprising anionic/amphoteric surfactant systems. Addition of specific EO-PO copolymers wherein ratio of anionic to EO-PO polymer is defined has been found to remarkably enhance mildness. In a second embodiment, the invention relates to a method for enhancing mildness in liquid detergent compositions comprising anionic surfactant by adding said defined EO-PO polymers.

8 Claims, 4 Drawing Sheets

LIQUID COMPOSITIONS COMPRISING COPOLYMER MILDNESS ACTIVES

FIELD OF THE INVENTION

The present invention relates to liquid personal wash compositions (e.g., shower gels), particularly compositions comprising (1) one or more anionic surfactants and (2) one or more amphoteric surfactants. The invention relates to the incorporation of specific polyoxyethylene (EO)—polyoxypropylene (PO) copolymers int he liquids. Through careful balancing of anionic surfactant to nonionic copolymer and specific selection of the nonionic copolymer, enhanced mildness is obtained.

BACKGROUND

The use of EO-PO polymer in liquid personal wash compositions is not new.

German Patent No. DE 2,409,081 (assigned to BASF), for example, teaches cleaning compositions comprising 5% to 40% amphoteric tenside and 15% to 40% EO-PO-EO block copolymer. No anionic surfactant is used in these compositions. Similarly, German Patent DE 3,113,790 (assigned to Wella AG) teaches hair and body compositions comprising 5 to 20% amine oxide, 1 to 9% fatty acid and 1 to 9% EO-PO-EO polymer, but no anionics are included.

French Patent FR 2,336,475 teaches aqueous shampoo compositions containing anionics but imidoziline ampholytic surfactant and nonionic surfactant are the primary cleanser.

U.S. Pat. No. 4,166,845 to Hansen et al. teach anti-dandruff shampoos containing 14 to 25% betaine, 1 to 6% supplementary (ionic) surfactants and 2 to 8% nonionics which include EO-PO copolymers. Again, anionic is not the primary cleaner.

U.S. Pat. No. 5,030,374 to Tranner teach gel facial cleansing formulations with 2% to 18% EO-PO copolymers as mild cleanser. No anionics or amphoterics are used.

U.S. Pat. No. 5,182,105 to Takata et al. teach bathing compositions containing an oily component, nonionic surfactants (which can be EO-PO copolymers) and cationic. EP 617,955 (assigned to Kao) teaches a mixture of nonionics in which fatty acid monoglyceride is used to increase foamability.

GB 2,181,737 (Aven Medical Ltd.) teaches liquid shampoos containing 10–15% tergobetaine, 3–8% nonionic (Pluronic) and 2–3% distearate thickener. Preferably, anionics are not used.

U.S. Pat. No. 4,126,674 to Mausner teaches a 2-in-1 shampoo with anionic/nonionic surfactant ratio of 30:0.9 to 3:0.9. The nonionic can be EO-PO-EO or other ethoxylated surfactants. No amphoteric is used (as required by the subject invention) and EO-PO-EO polymer is not specified. The copolymer of the subject invention must have percentage of EO greater than 50%, an HLB greater than 12 and must have MW of 6,000 to 25,000.

U.S. Pat. No. 4,664,835 to Grollier et al. (L'Oreal) teaches a washing agent containing mild nonionic and anionic surfactants and anionic polymer. Surfactant can be an EO-PO polymer. No amphoteric is exemplified and no ratio of anionic/EO-PO is specified.

U.S. Pat. No. 4,917,823 to Maile, Jr. (P&G) teach liquid cleaning compositions containing cellulose thickener, 0.5–20% solvent and to 50% surfactant. Solvent can be EO-PO polymer and surfactants are broadly disclosed. There is no teaching, however, of anionic/EO-PO ratio or of the specific EO-PO polymers of the invention.

Finally, U.S. Pat. Nos. 5,380,756; 5,378,731; and 5,219,887 teach disinfecting shampoos containing 20%–70% cleanser selected from EO-PO copolymers and other nonionic and anionic surfactants. No anionic/nonionic ratios are specified and no amphoteric surfactants appear to be disclosed.

In summary, none of the references, alone or in combination teach that the use of relatively low levels of specific EO-PO surfactant polymers (e.g., having specific HLB specific MW, and specific amount of EO as percentage of the copolymer) in specific surfactant systems (containing greater than or equal to 50% anionic surfactant(s); and also necessarily containing at least some amphoteric surfactant) will result in enhanced mildness of the specific systems.

BRIEF SUMMARY OF THE INVENTION

Unexpectedly, applicants have found that in liquid personal wash compositions comprising a surfactant system comprising:

(1) 3% to 30%, preferably 5% to 20%, total composition anionic surfactant or mixture of anionic surfactants, wherein anionic is greater than or equal to 50% of the surfactant system; and (2) 0.1 to 20% by wt. total composition one or more amphoteric surfactants, the addition of 0.1 to 25% by wt. composition EO-PO polymers (ratio of anionic to polymer being 1:1 to 10:1), wherein the polymer has HLB greater or equal to 12, preferably greater than 18 and wherein weight of EO portion is greater than or equal to 50%, preferably 60–85% of the weight of the copolymer, will lead to significantly enhanced mildness in such compositions.

The copolymers should have MW of 6,000 to 25,000, preferably 8,000 to 20,000. In addition EO terminated polymers are preferably PO terminated.

DETAILED DESCRIPTION OF THE INVENTION

Figure 1A:
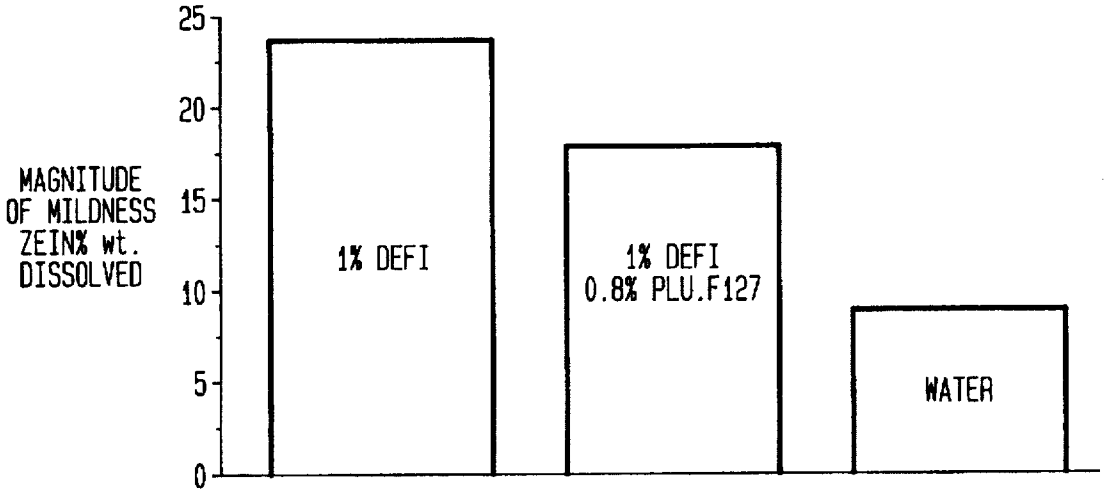
FIG. 1 shows the effect of the EO-PO nonionic surfactant polymers on zein normally dissolved by acyl isethionate (DEFI). The greater the zein dissolved, the harsher is the surfactant generally considered to be. The polymers of the invention reduce the zein dissolved (i.e., increase mildness) over DEFI alone (FIG. 1A); enhance mildness when used with DEFI relative to polyethylene glycol and DEFI (FIG. 1B); and even significantly enhance mildness in an isethionate/betaine system (very mild) compared to PEG used in the same system (FIG. 1C).

The present invention relates to novel liquid personal water compositions, particularly compositions in which the surfactant system comprises greater than 50% of the surfactant system anionic surfactant or surfactants, and additionally comprises one or more amphoteric surfactants.

Unexpectedly, applicants have found that when relatively small amounts (0.1 to 20% by wt. composition) of a defined EO-PO polymer (i.e., defined by MW of 6,000–25,000; HLB$\geqq$12; and by percentage of EO of copolymer being $\geqq$50% to 90% if copolymer) is used, and when there is a defined ratio of anionic to EO-PO polymer (i.e., 1:1 to 10:1), the liquid composition is significantly milder (as defined by zein dissolution and patch tests) than either in the absence of the polymer or if a different alkylene oxide (e.g., polyethylene oxide) is used.

The compositions are defined in greater detail below:

Surfactant System

The surfactant system of the subject invention generally comprises 5 to 50% by weight, preferably 10 to 40% by wt. of the composition and comprises:

(a) 3% to 30%, preferably 5 to 20% by wt. total composition one or more anionic surfactants wherein the anionic surfactant comprises 50% or more of the surfactant system;

(b) 0.1 to 20% by wt., preferably 3% to 10% total composition amphoteric and/or zwitterionic surfactant; and (c) 0% to 10% optional nonionic surfactant (other than EO-PO polymer of invention).

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation;

amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

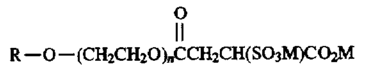

wherein n=1 to 20; and M is as defined above.

Sarcosinates are generally indicated by the formula $$RCON(CH_3)CH_2CO_2M,$$

wherein R ranges from $C_8$–$C_{20}$ alkyl and M is a solubilizing cation.

Taurates are generally identified by formula $$R^2CONR^3CH_2CH_2So_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

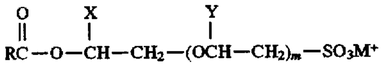

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 20% by weight of the composition, preferably 5 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group,e.g., carboxy, sulfonate,sulfate, phosphate, or phosphonate. A general formula for these compounds is:

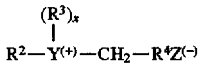

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

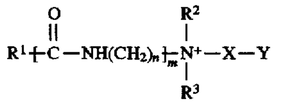

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

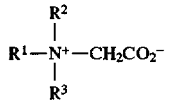

and amido betaines of formula:

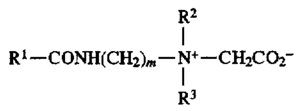

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

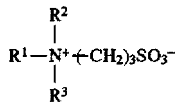

or

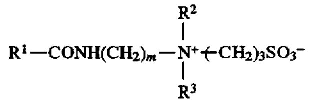

where m is 2 or 3, or variants of these in which $—(CH_2)_3SO^-_3$ is replaced by

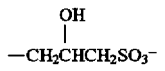

In these formulae $R^1$, $R^2$ and $R^3$ are as discussed previously.

A further possibility is that the amphoteric detergent is a sulphobetaine of formula

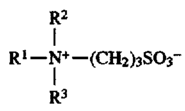

or

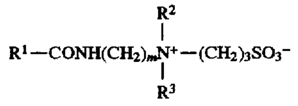

where m is 2 or 3, or variants of these in which $—(CH_2)_3SO_3^-$ is replaced by

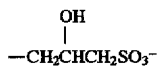

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 0.1% to 15%, more preferably 0.1 to 10% by wt. of the composition.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

EO-PO Polymer

The polyoxyethylene polyoxypropylene nonionic copolymers (EO-PO copolymers) of the subject invention are generally commercially available polymers having a broad molecular weight range and EO/PO ratio and a melting temperature of from about 25° to 85° C., preferably 400° to 65° C.

Generally, the polymers will be selected from one of two classes of polymers, i.e., (1) $(EO)_m(PO)_n(EO)_m$ type copolymers or $(PO)_n(EO)_m(PO)_n$ type copolymers of defined m/n ratio and optional hydrophobic moieties (e.g., decyltetradecanol ether) attached to either EO or PO compounds (such products are commercially available for example, from BASF under the Trademark Pluronic® or Pluronic-R®, respectively); or (2) EO-PO polymers with amine constituents such as $N_2C_2H_4(PO)_{4n}(EO)_{4m}$ or $N_2C_2H_4(EO)_{4m}(PO)_{4n}$ with defined values of m and n and optional hydrophobic moieties attached to either EO or PO components (such products are commercially available, for example from BASF as Tetronic® and Tetronic-R®, respectively).

Specifically, examples of various Pluronic and Tetronic EO-PO polymers are set forth in Table 1 below wherein $T_m$ (°C.) and Ross Miles foam height data (measured at 0.1% and 50° C.) were digested from literature from BASF.

TABLE 1

| Polymer | | $T_m$(°C.) | Foam Heights (ml) | EO and PO Number |
|---|---|---|---|---|
| Pluronic: | $(EO)_m$—$(PO)_n$—$(EO)_m$ | | | m/n |
| | F38 | 48 | 35 | 46/16 |
| | F68 | 52 | 35 | 75/30 |
| | F77 | 48 | 47 | 52/35 |
| | F87 | 49 | 44 | 62/39 |
| | F88 | 54 | 48 | 97/39 |
| | F98 | 58 | 43 | 122/47 |
| | F108 | 57 | 41 | 128/54 |
| | F127 | 56 | 41 | 98/67 |
| Pluronic-R: | $(PO_n$—$(EO)_m$—$(PO)_n$ | | | |
| | 10R8 | 46 | 20 | 90/9 |
| | 17R8 | 53 | 2 | 155/15 |
| | 25R8 | 54 | 15 | 227/21 |
| Tetronic: | $N_2C_2H_4$—$(PO)_{4n}(EO)_{4m}$ | | | |
| | 707 | 46 | 60 | 35/12 |
| | 1107 | 51 | 50 | 64/20 |
| | 908 | 58 | 40 | 85/16 |
| | 1307 | 54 | 40 | 78/25 |
| | 1508 | 60 | 40 | 159/30 |
| Tetronic-R: | $N_2C_2H_4$—$(EO)_{4m}(PO)_{4n}$ | | | |
| | 90R8 | 47 | 0 | 90/17 |
| | 110R7 | 47 | 0 | 64/21 |
| | 150R8 | 53 | 0 | 12/29 |

In general, the molecular weight of the copolymers used ranges from 6,000 to 25,000 (preferably 8,000 to 20,000). The EO-terminated polymers (Pluronic and Tetronic) are preferred to the PO-terminated ones (pluronic-R and Tetronic-R) for the advantages of mildness enhancement and lather generation.

In a preferred embodiment, the portion of ethylene oxide moiety per mole should be between 50% to 90% wt., more preferably 60–85% wt. In other words, 2 m:n (for Pluronic)

or m:n (for Tetronic) ranges from 1.32 to 11.9, preferably 2.0 to 7.5. It is believed that this will ensure solubility of the polymer.

In a related manner (i.e.,related to solubility), the hydrophilic-lipophilic balance should preferably be greater than 12, preferably greater than 18. The hydrophobic-hydrophilic balance is calculated from GLC (gas liquid chromatography) relative retention ratios and value, are as described in catalogs from BASF (e.g., BASF Performance Chemicals Catalog describing Pluronic® Tetranic® and other copolymers, published in 1991 by BASF Corporation).

In addition, the ratio of anionic polymer to EO-PO polymer should be in the range of 1:1 to 10:1, preferably 1:1 to 10:3. While not wishing to be bound by theory, this ratio is believed critical because, at ratios above 10:1, improvement on mildness is not significant and, at ratios below 1:1, foaming and rheological properties are negatively affected.

The EO-PO polymer generally comprise 0.1 to 20% by wt. of the liquid composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330—Polyquaternium 39; and Jaguar® type conditioners.

Polyethylene glycols which may be used include:

Polyox WSR-205 PEG 14M,

Polyox WSR-N-60K PEG 45M, or

Polyox WSR-N-750 PEG 7M.

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut shells and apricot seeds The compositions may also contain 0.1 to 15% by wt., preferably 1 to 10% by wt. of a structurant. Such structurants can be used to avoid addition of external structurants (e.g., cross linked polyacylates and clays) if suspending particles is desired as well as to provide desirable consumer attributes.

The structurant is generally an unsaturated and/or branched long chain ($C_8$–$C_{24}$) liquid fatty acid or ester derivative thereof; and/or unsaturated and/or branched long chain liquid alcohol or ether derivatives thereof. It may also be a short chain saturated fatty acid such as capric acid or caprylic acid. While not wishing to be bound by theory, it is believed that the unsaturated part of the fatty acid of alcohol or the branched part of the fatty acid or alcohol acts to "disorder" the surfactant hydrophobic chains and induce formation of lamellar phase.

Examples of liquid fatty acids which may be used are oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Examples of alcohols include oleyl alcohol and isostearyl alcohol. Examples of ether derivatives include isosteareth or oleth carboxylic acid; or isosteareth or oleth alcohol.

The structuring agent may be defined as having melting point below about 25° C. centigrade.

Another optional ingredient is oil/emollient which may be added as a benefit agent to the liquid compositions.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) should not comprise more than 20%, preferably no more than 15% of the composition.

The emollient/oil is generally used in an amount from about 1 to 20%, preferably 1 to 15% by wt. of the composition. Generally, it should comprise no more than 20% of the composition.

The following examples are intended to illustrate further the invention and are not intended to limit the invention in any way.

All percentages are intended to be percentages by weight unless stated otherwise.

EXAMPLES

Protocol

Mildness Assessments: Zein dissolution test was used to preliminary screen the irritation potential of the formulations studied. In an 8 oz. jar, 30 mLs of an aqueous dispersion of a formulation were prepared. The dispersions sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

The Protocol of 3-Day Patch Test

Patch test was used to evaluate skin mildness of aqueous dispersions containing 1% DEFI active (sodium cocoyl isethionate) and different levels of the structurant/coactives. Patches (Hilltop® Chambers, 25 mm in size) were applied to the outer upper arms of the panelists under bandage type dressings (Scanpor® tape). After each designated contact periods (24 hrs. for the first patch application, 18 hrs. for the second and third applications), the patches were removed and the sites were visually ranked in order of severity (erythema and dryness) by trained examiners under consistent lighting.

Formulation Processing: Formulations shows in the examples of this invention were prepared in 400 mL beakers in a 40–60 C. oil bath. Mixing was accomplished with a variable speed overhead motor. Batch size was varied from 100–250 gms. All chemicals used were commercial materials and used as supplied. Those chemicals were dispersed in Milli-Q water, which accounted for 50–80% of the whole formulation. After the batch was homogeneously mixed, it was allowed to be cooled under room temperature.

Example 1

Figure 1B:
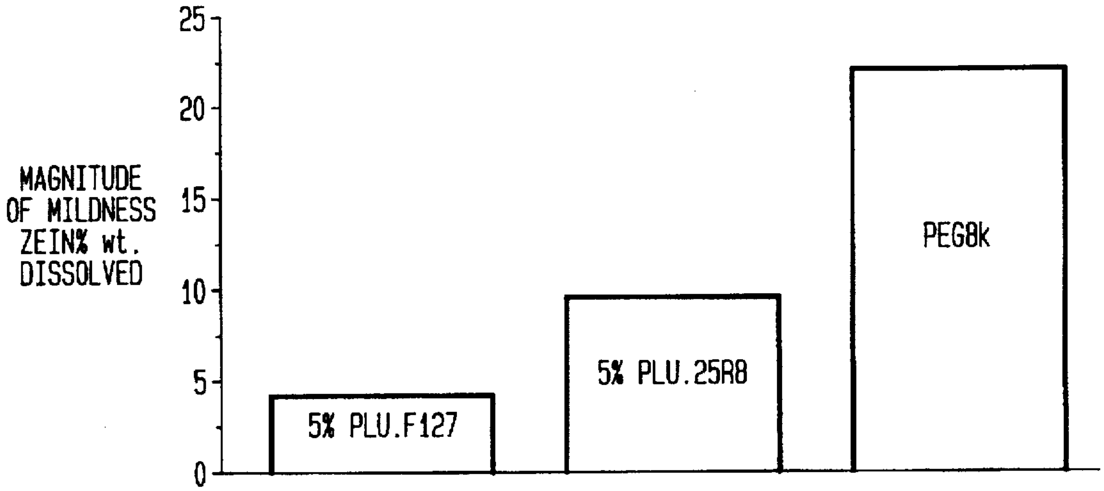
Figure 1C:
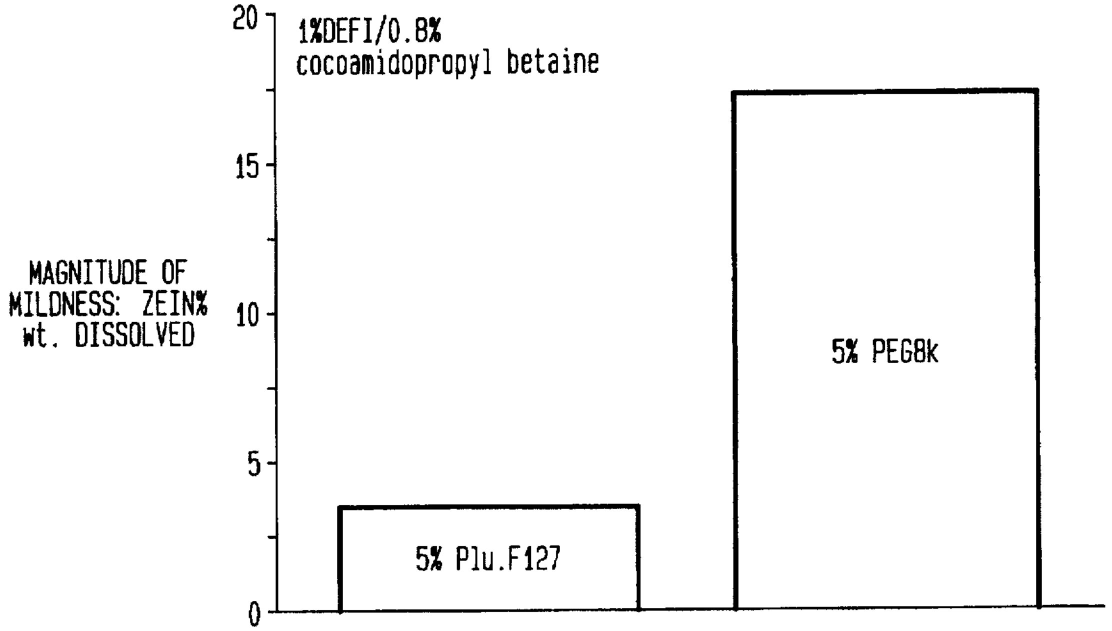

The irritation reduction potential of Pluronics was investigated using Zein dissolution experiments. Results in FIG. 1(*a,b*) indicated that Pluronic surfactants as a class are significantly more effective than PEG 8000 in reducing the Zein % dissolved by a 1% aqueous DEFI suspension (DEFI is a sodium acyl isethionatelfatty acid mixture containing about 75% sodium acyl isethionate, 23% stearic, palmitic acid and small amounts of minors (e.g., sodium isethionate). FIG. 1(*b*) also showed that EO-terminated Pluronic F127 is potentially a better mildness enhancer than the PO-terminated Pluoronic 25R8. FIG. 1(*c*) showed that EO-PO can significantly reduce the Zein % dissolved by even a quite mild detergency system (DEFI/cocoamidopropyl betaine).

Example 2

Figure 2:
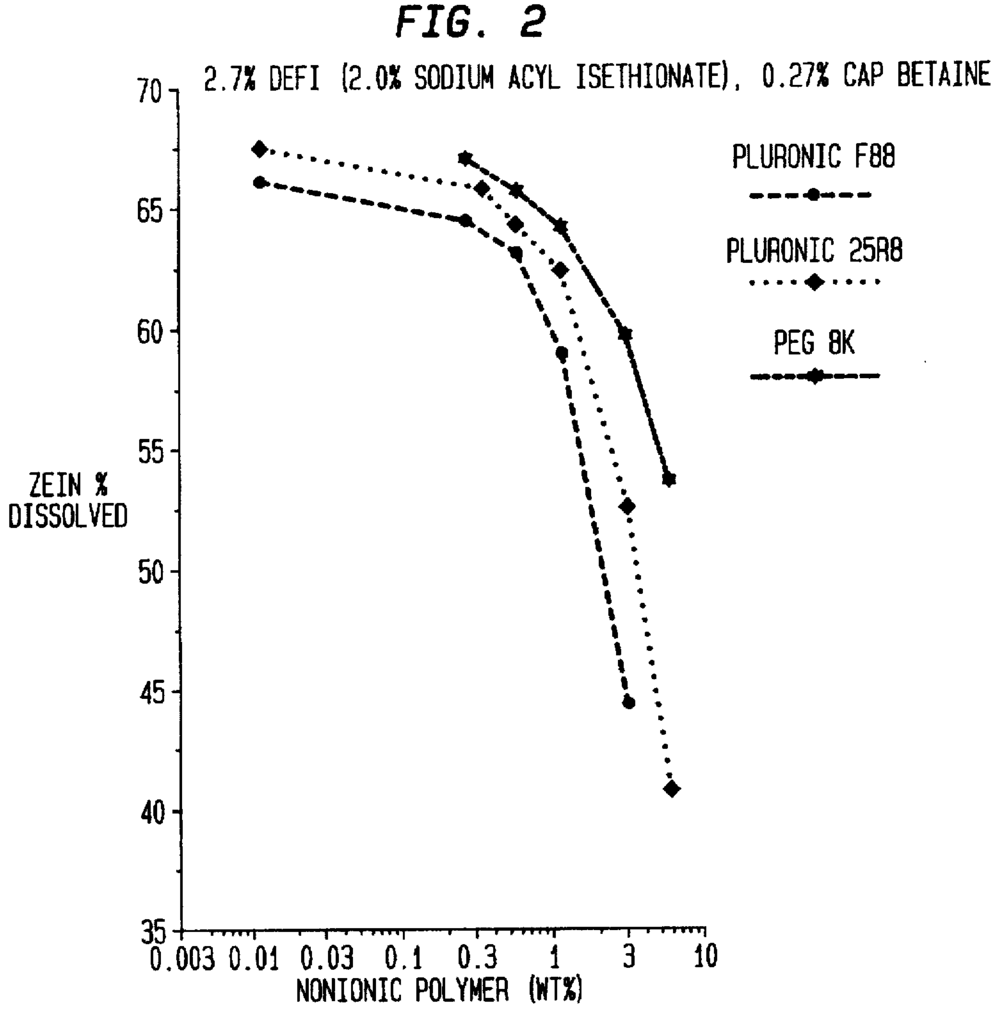
FIG. 2 shows dose response (i.e., how much of the polymer surfactant is needed to reduce zein) of the polymer in an isethionate/betaine system.

FIG. 2 shows the Zein % dissolved by DEFI as a function of Pluronic concentration. In contrast to PEG 8000 (where 1% of higher, i.e., the equivalent of 15% or higher of total composition comprising 30% wt. anionic active, were needed to lower Zein scores), low levels of Pluronic F88 and 25R8 (i.e., about 0.3%, equivalent to about 4.5% in total composition comprising 30% by wt. anionic surfactant based on sodium acyl isethionate to EO-PO wt. ratio of 1:0.15) significantly reduced the Zein % dissolved. Therefore it is possible that the irritation potential of a liquid cleansing formulation can be further reduced by including even low levels of Pluronics in the formulation. The data also showed that EO-terminated Pluronic F88 is potentially a better mildness enhancer than the PO-terminated Pluronic 25R8.

Example 3

Figure 3:
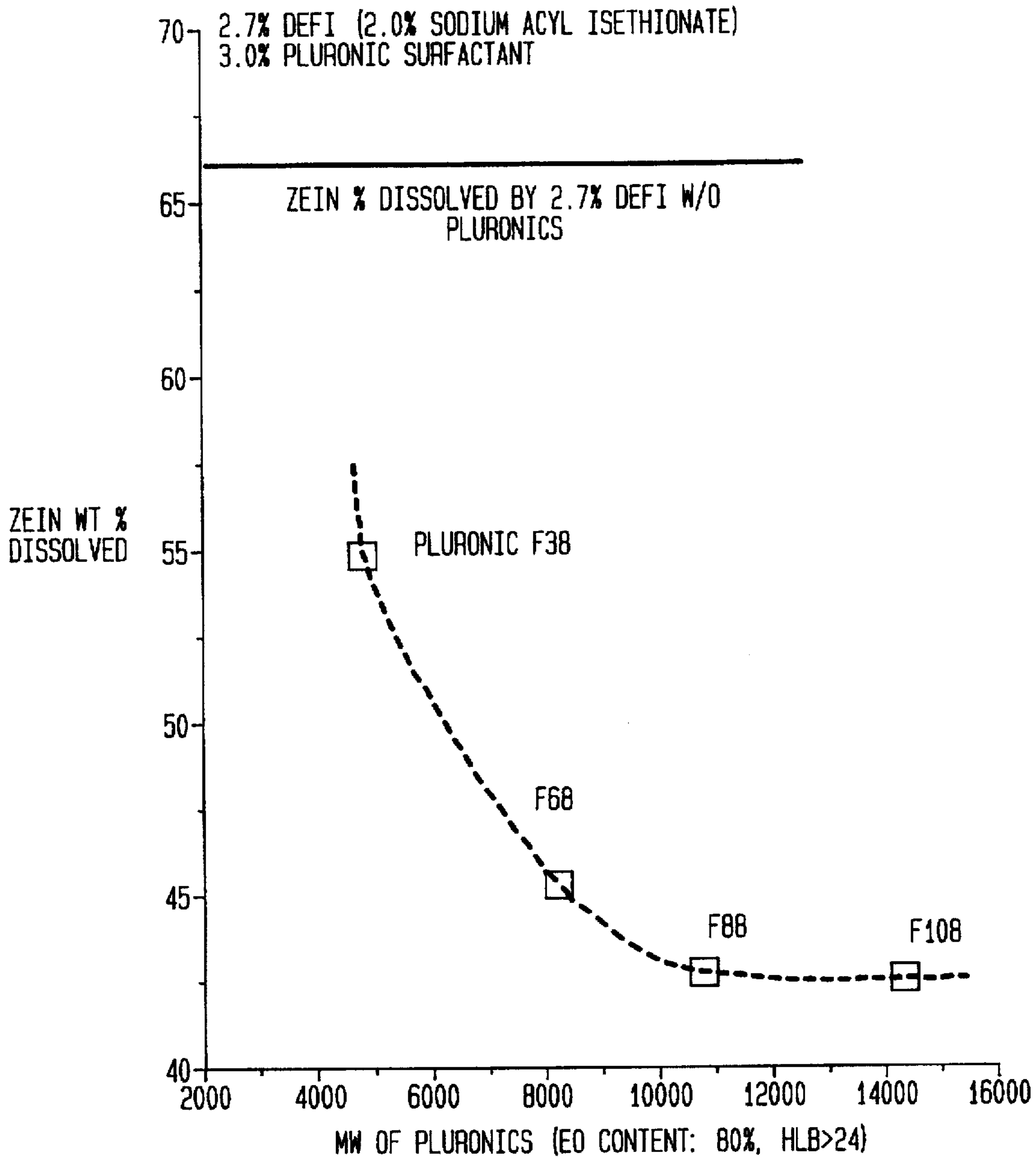
FIG. 3 shows the effect of the polymer depending on the molecular weight of the polymer. In general, as molecular weight increases, less zein is dissolved (milder). Zein dissolution is measured in an isethionate aqueous liquor.

FIG. 3 shows the Zein % dissolved by DEFI in the presence of different water soluble Pluronics (EO % equals 80%; HLB>24). The molecular weight of these Pluronics ranges from 4500 to 15000. The results indicated that the high molecular weight Pluronics (>8,000 Dalton) are significantly more effective than the low MW Pluronics in reducing the Zein % dissolved by DEFI. Therefore, the high MW, water soluble EO-PO copolymers are preferred to be included in personal washing formulations for the purpose of mildness enhancement.

Example 4

Figure 4:
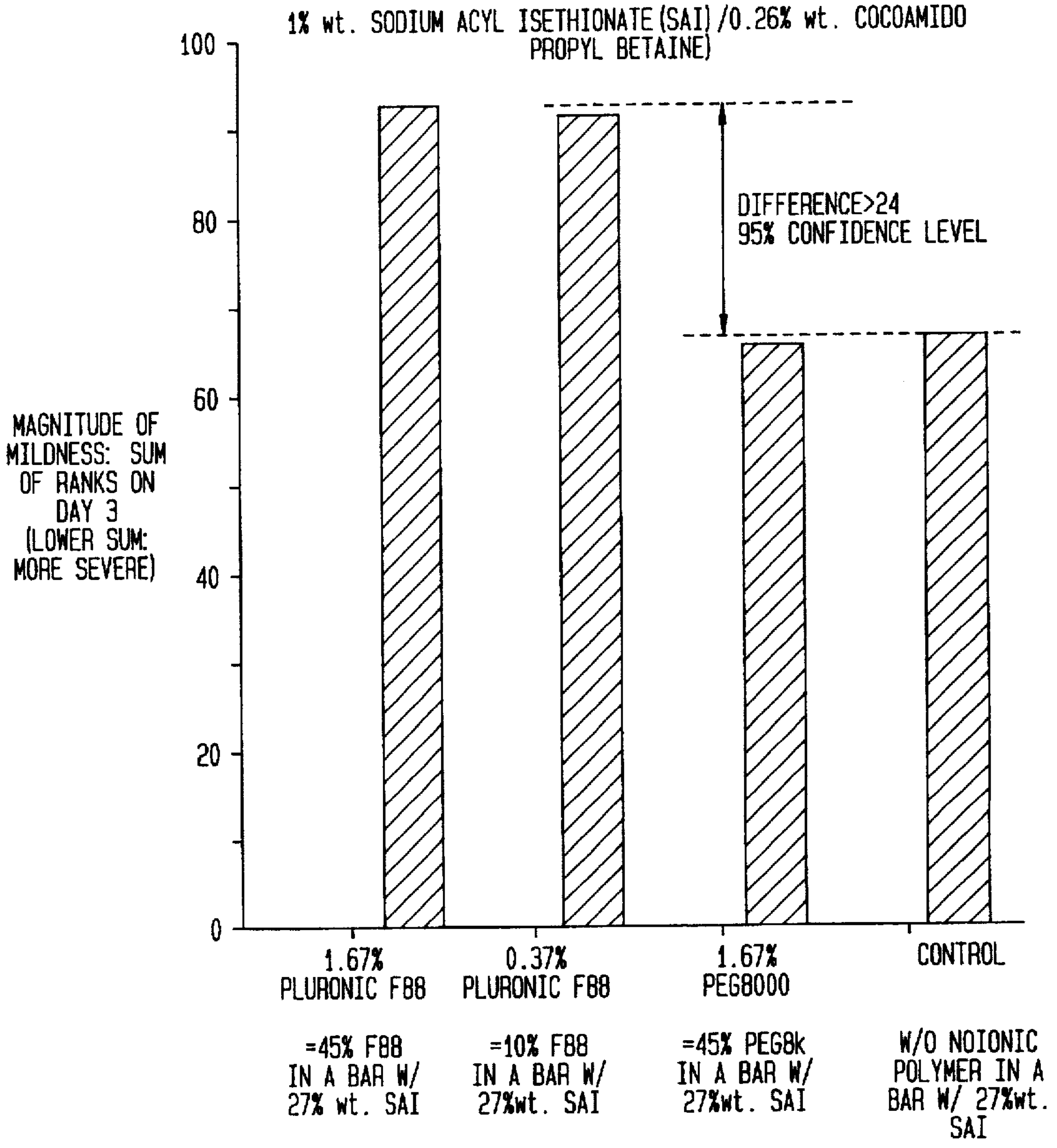
FIG. 4 shows mildness of polymers of the invention relative to polyethylene glycol in an isethionate betaine system. There, the higher score refers to enhanced mildness.

Patch test indicate that Pluronic F88 significantly reduced the skin erythema/edema caused by DEFI. As shown in FIG. 4, at sodium acyl isethionate (SAI) to F88 weight ratio as high as 1:0.37 (equivalent to the SAI/F88 ratio in the Formulation C of Example 6), Pluronic F88 significantly reduced the skin irritation of a DEFI/betaine liquor. In contrast,even at SAI/PEG 8000 weight ratio as low as 1:67 (effectively 25% PEG 8,000 in the Formulation C of Example 6), PEG 8000 made no measurable mildness contribution to the DEFI/betaine aqueous liquor.

Example 5

Zein dissolution experiments (Table 2) revealed that Pluronic F88 can significantly reduce the amount of Zein dissolved by many different types of anionic surfactants commonly used in personal washing products. Thus inclusion of those water soluble EO-POs in the liquid formulations containing the anionic surfactant listed in Table 2 can effectively enhance the mildness of the liquid cleansing formulations.

TABLE 2

| Formulation (in distilled water) | | Zein % dissolved (w/w) |
|---|---|---|
| Anionic surfactant | Pluronic F88 | (standard dev. < 2%) |
| 1% sodium lauryl sarcosinate | 0.73% | 37.1% |
| 1% sodium lauryl sarcosinate | 0 | 43.8 |
| 1% SLES (3EO) | 0.73% | 28.6 |
| 1% SLES (3EO) | 0 | 35.8 |
| 1% sodium lauryl sulfate | 0.73% | 59.9 |
| 1% sodium lauryl sulfate | 0 | 66.9 |
| 1% sodium soap (82:18 tallowate/cocoate) | 0.73% | 38.5 |
| 1% sodium lauryl isethionate | 0 | 46.5 |

Example 6

All amounts are given in percentage of weight. These formulations used sodium cocoyl isethionate as the major anionic detergent with other amphoteric and anionic surfactants as coactives. The formulation (A) was a stable milky white cream, which provided rich, creamy, and slippery lather that was rinsed off easily. The formulation (B) and (C) were stable milky white lotions that were pourable and pumpable. These lotions provided rich and creamy lather.

TABLE 3

| Formulation | (A) | (B) | (C) |
|---|---|---|---|
| Sodium cocoyl isethionate (From DEFI*) | 0 | 0 | 14.5% |
| Sodium cocoyl isethionate (From IGEPON AC-78) | 10.0% | 9.0% | 0.0 |
| Cocoamidopropyl betaine | 5.0 | 4.5 | 3.8 |
| Sodium lauryl ether sulphate, 3EO | 0.0 | 1.8 | 4.8 |
| Glycerin | 0.0 | 1.4 | 1.0 |
| Palmitic-stearate acid (From IGEPON or DEFI) | 0.4 | 0.4 | 4.5 |
| Pluronic F88 | 10.0 | 4.5 | 5.4 |
| Tetronic 1107 | 0.0 | 4.5 | 0.0 |
| Propylene glycol | 0.0 | 4.8 | 0.0 |
| Sodium chloride | 2.0 | 1.8 | 1.4 |
| Ammonium chloride | 0.0 | 5.8 | 5.0 |
| Sodium isethionate | 0.4 | 0.4 | 0.2 |
| Water | balance to 100% | balance to 100% | balance to 100% |

*DEFI: directly esterified fatty acid isethionate, which is a mixture containing about 74% by weight of sodium acyl isethionate, 23% stearic-palmitic acid and small amounts of other materials, manufactured by Lever Brothers Co, U.S.

Example 7

All amounts are given in percentage of weight. These formulations used sodium lauryl sulphate. (3EO) as the major anionic detergent with optional amphoteric and anionic surfactants as coactives. These clear, free low liquids provided rich, creamy and slippery lather and smooth skin feel.

TABLE 4

| Formulation | (C) | (D) | (E) |
|---|---|---|---|
| SLES (3EO) | 5.0 | 10.0 | 15.0 |
| Sodium lauryl sarcosinate | 5.0 | 0.0 | 0.0 |
| Cocoamidopropyl betaine | 5.0 | 5.0 | 10.0 |
| Propylene glycol | 2.0 | 1.0 | 2.0 |
| Pluronic F88 | 5.0 | 10.0 | 10.0 |
| Water | Balance to 100% | Balance to 100% | Balance to 100% |

We claim:

1. A liquid detergent composition comprising:

(a) a detergent surfactant system comprising (1) 3% to 30% by wt. total composition anionic or mixtures of anionic surfactants wherein the anionic surfactant comprises 50% or greater of the detergent active system; and (2) 0.1% to 20% by wt. total composition comprising one or more amphoteric surfactants, and (b) 0.1 to 20% by wt. of a copolymer comprising both oxyethylene and oxypropylene groups;

wherein the ratio of anionic or anionics to copolymer comprising oxyethylene and oxypropylene groups is 1:1 to 10:1;

wherein the copolymer is defined by having a hydrophilic lipophilic balance (HLB) of >12; as having the percentage of ethylene oxide group comprising the copolymer being >50% to 90%; and as having a molecular weight of 6,000 to 25,000.

2. A composition according to claim 1, wherein the anionic surfactant or surfactants comprises 5% to 20% of the composition.

3. A composition according to claim 1, wherein amphoteric comprises 3% to 10% of the composition.

4. A composition according to claim 1, wherein HLB>18.

5. A composition according to claim 1, wherein Ethylene oxide groups comprises 60% to 85% of the copolymer.

6. A composition according to claim 1, wherein MW of copolymer is 8,000 to 2,000.

7. A composition according to claim 1, wherein the copolymer is terminated with an ethylene oxide group.

8. A method of enhancing mildness of a liquid detergent composition comprising a surfactant system comprising 3% to 30% by wt. anionic or mixture of anionics which method comprises adding 0.1 to 20% by wt. of a copolymer comprising ethylene oxide and propylene oxide groups to said composition;

wherein the ratio of anionic or anionics to copolymer is 1:1 to 10:1;

wherein the copolymer comprising ethylene oxide and propylene oxide groups is defined by having a hydrophilic lipophilic balance (HLB) of >12; as having the percentage of ethylene oxide groups comprising the copolymer being >50% to 90%; and as having a molecular weight of 6,000 to 25,000.

* * * * *